United States Patent [19]

Wagle et al.

[11] 4,075,236

[45] Feb. 21, 1978

[54] CONTINUOUS MANUFACTURE OF PEROXYESTERS

[75] Inventors: Uday Dakornath Wagle, Grand Island; Venkatram Ramdas, Tonawanda, both of N.Y.

[73] Assignee: Pennwalt Corporation, Philadelphia, Pa.

[21] Appl. No.: 728,349

[22] Filed: Sept. 30, 1976

[51] Int. Cl.² ........................................... C07C 179/18
[52] U.S. Cl. ............................................. 260/453 RZ
[58] Field of Search .................. 260/453 RZ, 410.9 R

[56] References Cited

U.S. PATENT DOCUMENTS

| | | |
|---|---|---|
| 3,082,236 | 3/1963 | Mogeli et al. ................. 260/453 RZ |
| 3,117,166 | 1/1964 | Harrison et al. .............. 260/453 RZ |
| 3,435,060 | 3/1969 | Johannes ........................ 260/453 RZ |
| 3,849,468 | 11/1974 | Busseret ............................... 260/463 |
| 3,869,489 | 3/1975 | Tiquet et al. ................... 260/453 RZ |

*Primary Examiner*—Joseph P. Brust
*Assistant Examiner*—Robert C. Whittenbaugh

[57] ABSTRACT

A continuous solvent-free process for the manufacturing of peroxyesters from an acid chloride, a hydroperoxide and an alkali metal hydroxide generates a pure product of good quality, high yields and throughput per unit volume of the reactor. The process comprises at least two reactors and a physical separation unit for separating the high purity product.

9 Claims, 1 Drawing Figure

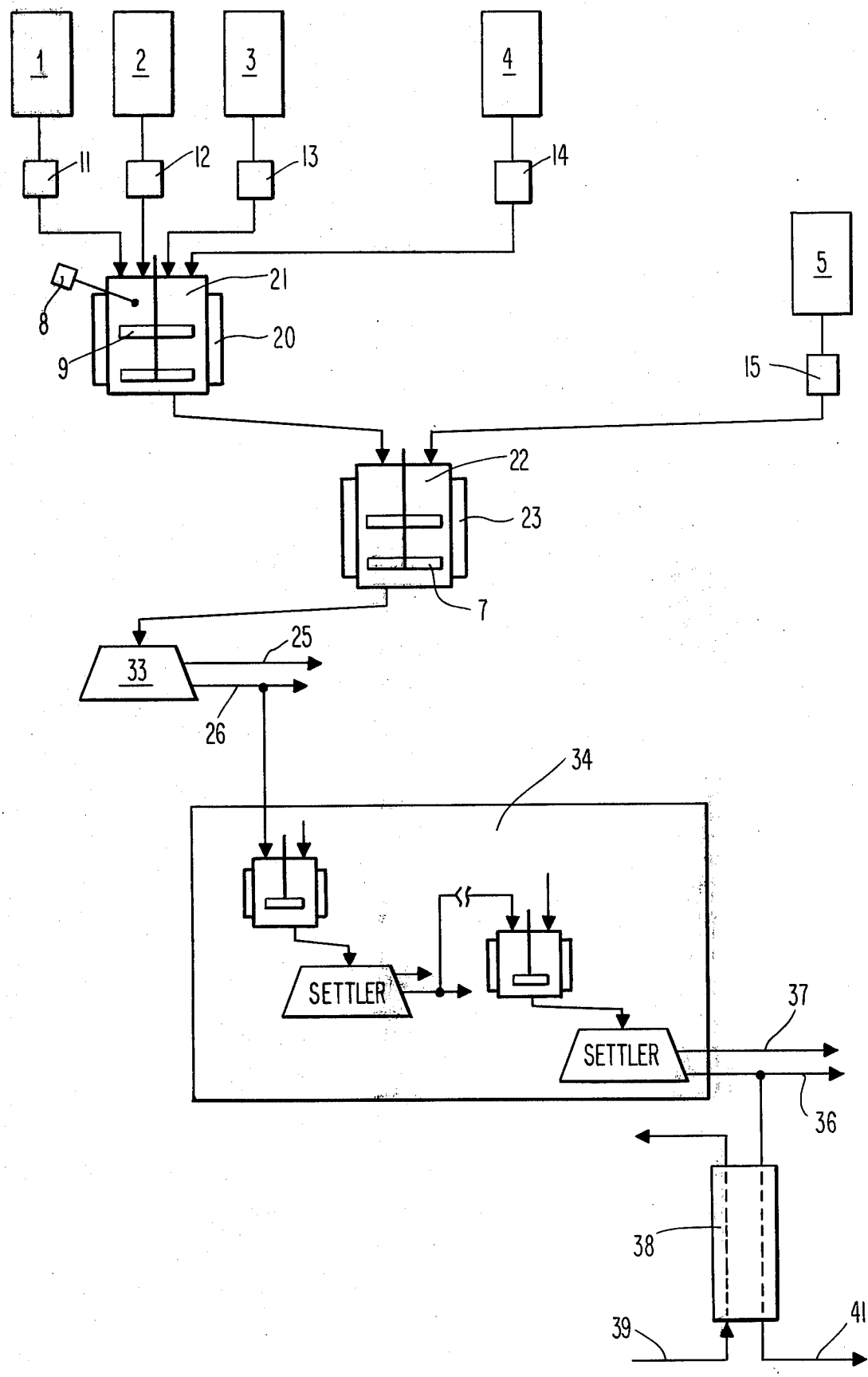

CONTINUOUS MANUFACTURE OF PEROXYESTERS

BACKGROUND OF THE INVENTION

1. FIELD OF INVENTION

This invention concerns a process and apparatus for the continuous manufacture of peroxyesters in high purity and at high through put per unit reactor volume.

2. STATE OF THE PRIOR ART

Peroxyesters, R-C(O)OOR', are extensively used as initiators in the polymerization field because they are efficient initiators. These peroxyesters, however, are highly temperature sensitive decomposing violently to the point of ignition at high temperatures. The presence of a large amount of peroxyester in a reaction mass only augments this problem; hence, extreme precautions are necessary to prevent accidents in the commercial batch processes when large quantities of the peroxyesters are produced. One precaution usually exercised in the preparation of peroxyesters is to use a solvent medium to ensure safe operation. The presence of solvents in the initiators, however, often affect their efficiency adversely in the polymerization processes.

An example of the prior art is U.S. Pat. No. 3,849,468 which describes a continuous process for the preparation of solutions of tertiary-butyl peroxyesters in a single closed-circuit reactor system; the acid chloride, the caustic, the t-butyl hydroperoxide and solvent are introduced into the system in the presence of an aqueous reaction support. In the system described, air is used to promote circulation of material in the closed loop. The mixing and interfacial contact between the reactants in the two phases are brought about by passing them and the reaction support through a packed column of Raschig rings. Such a system is inadequate for the efficient mixing essential for ensuring complete conversion of the acid chlorides, particularly the high molecular weight ones that are sluggish to react; hence this would result in an impure product containing a significant amount of the unreacted acid chloride. Also the presence of the reaction support decreases the effective volume for the reaction thereby reducing the throughput per unit volume of the reactor.

Since the use of solvents and aqueous reaction support decreases the efficiency of processing and since pure (undiluted) peroxyesters are desired for many polymerization processes, it would be highly desirable to have a continuous, solvent-free process which would increase processing efficiency yielding products of high quality at high throughputs and be capable of providing the polymerization industry with a choice of either pure or diluted products.

SUMMARY OF THE INVENTION

According to this invention there is provided an improved, solvent-free process for the continuous manufacture of peroxyesters having the general structure $R_y\text{-(C(O)OO)}_n R'_{xx}$, wherein:

(a) $x$, $y$, and $n$ are 1 or 2;
(b) when $x$ is 2, $y$ is 1 and $n$ is 2;
(c) when $y$ is 2, $x$ is 1 and $n$ is 2;
(d) when $x$, $y$ and $n$ are 1, p is selected from the group consisting of a primary, secondary or tertiary alkyl of 1 to 17 carbons, aryl or substituted aryl of 6 to 14 carbons, and cycloalkyl of 3 to 12 carbons, and R' is selected from the group consisting of a tertiary alkyl of 4 to 12 carbons, a tertiary aralkyl of 9 to 18 carbons, and tertiary cycloalkyl of 6 to 12 carbons;
(e) when $x$ is 2, R is a diradical selected from alkylene of 1 to 16 carbons, arylene of 6 to 14 carbons, cycloalkylene of 3 to 12 carbons, and aralkylene of 7 to 18 carbons;
(f) when $y$ is 2, R' is a di-tertiary diradical selected from alkylene of 6 to 16 carbons, aralkylene of 12 to 18 carbons, and cycloalkylene of 7 to 12 carbons.

The peroxyesters are produced by continuously reacting an acid chloride having the formula

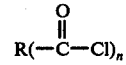

with a hydroperoxide having the formula $R'(-OOH)_n$ and an aqueous alkali metal hydroxide in at least two reaction zones connected in series of intense mixing in a temperature range of about $-10°$ to $+50°$ C and a pH greater than 10. Continuously feeding the reaction mixture directly from the last of the reaction zones through a separation device such as a centrifuge or a gravity settling unit to isolate the peroxyester product (the organic phase) in at least about 95% purity (assay). Optionally, the purity can be further improved to greater than 97% by subjecting the isolated organic phase to a series of washes followed by physical separations. A higher purity, greater than 98–99% in assay and low moisture content (less than 500 ppm), can be obtained by continuously passing the organic phase from the last separation device through a stripping zone where the product is subjected to stripping with dry air in a stripping column.

DETAILED DESCRIPTION OF THE INVENTION

It has now been discovered that peroxyesters can be continuously produced at a high throughput per unit reactor volume, safely and in high purity in an efficient, solvent-free process by employing at least two vigorous mixing reaction zones and physical separation units such as centrifuges or gravity settling columns to isolate pure product. The peroxyester is generated by continuously reacting an acid chloride, a hydroperoxide, and an alkali metal hydroxide in at least two reacting zones of intense mixing in a temperature range of $-10°$ to $+50°$ C and at a pH greater than 10.

Examples of the acid chlorides, $R(C(O)Cl)_n$, useful in the process of this invention are:

(a) In the preparation of monoperoxyesters (that is $x$, $y$ and $n = 1$); acetyl (R = methyl), propionyl (R = ethyl), butyryl (R = propyl), pentanoyl or valeroyl (R = butyl), 2-ethylhexanoyl (R = 3-heptyl), isobutyryl (R = isopropyl), 2-methylbutyryl (R = sec-butyl), 2-methyl-pentanoyl (R = 2-pentyl), 2-ethylbutyryl (R = 3-pentyl), neodecanoyl (R = tertiary-nonyl), decanoyl (R = nonyl), lauroyl (R = undecyl), benzoyl (R = phenyl), toluoyl (R = methylphenyl), isononanoyl (R = 2,4,4-trimethylpentyl), napthoyl (R = napthyl), and pivaloyl (R = tertiary-butyl).

(b) In the preparation of diperoxyesters (that is $x = 2$, $y = 1$, $n = 2$ and R is a diradical); malonyl (R = methylene), succinoyl (R = ethylene), glutaroyl (R = trimethylene), adipoyl (R = tetramethylene), azclaoyl (R = heptamethylene), sebacoyl (R = octamethylene), phthaloyl (R = o, m, p-phenylene) and fumaroyl (R = ethenylene).

Examples of hydroperoxides R'(OOH)$_n$ useful in the process of this invention are:

(a) In the preparation of monoperoxyesters that is $x$, $y$ and $n = 1$ wherein the radical R' and the hydroperoxide have the same name, t-butyl, t-amyl, t-hexyl, t-heptyl, t-octyl, cumyl, p-phenylcumyl, p-menthane (p-menthanyl), pinane (pinanyl), 1-methylcyclopentyl, and 1-methylcyclohexyl hydroperoxides;

(b) In the preparation of diperoxyesters that is $y = 2$, $x = 1$, $n = 2$ and R' is a diradical; 2,5-dimethyl-2,5-dihydroperoxy hexane (R' = 1,1,4,4 tetramethyltetramethylene), 2,7-dimethyl-2,7-dihydroperoxyoctane (R' = 1,1,6,6-tetramethylhexamthylene), 3,6-dimethyl-3,6-dihydroperoxyoctane (R' = 1,4-dimethyl-1,4-diethyltetramethylene), 2,5-dimethyl-2,5-dihydroperoxyhexyne-3 (R' = 1,1,4,4 tetramethyl-2-butynylene), and diisopropylbenzene dihydroperoxide (R' = α,α, α',α'-tetramethylxylylidene).

Examples of the alkali metal hydroxide used in the reactions are sodium hydroxide and potassium hydroxide.

Illustrative of but not limiting of the various peroxyesters able to be prepared by the process of the invention are:

t-butylperoxyacetate, cumylperoxyacetate,
t-butylperoxyisobutyrate, cumylperoxyisobutyrate,
t-butylperoxypivalate, cumylperoxypivalate,
t-butylperoxy 2-ethylhexanoate, cumylperoxy 2-ethylhexanoate,
t-butylperoxyneodecanoate, cumylperoxyneodecanoate,
t-butylperoxybenzoate, cumylperoxybenzoate,
di-t-butyl diperoxyphthalate,
di-t-butyl diperoxymalonate, di-t-butyl diperoxysuccinate,
di-t-butyl diperoxyglutarate, di-t-butyl diperoxyadipate,
di-t-butyl diperoxyazelate, di-t-butyl diperoxysebacate,
di-t-butyl diperoxyfumarate,
2,5-dimethyl-2,5-di(2-ethylhexanoylperoxy) hexane,
2,5-dimethyl-2,5-di(pivaloylperoxy) hexane,
2,5-dimethyl-2,5-di(neodecanoylperoxy) hexane,
2,5-dimethyl-2,5-di(benzoylperoxy) hexane,
2,5-dimethyl-2,5-di(2-ethylhexanoylperoxy) hexyne-3, and
1,4 di [α,α-dimethyl-α-(t-butylperoxycarbonyl)-methyl] benzene.

Optionally, a diluent can be added to the mixing zone to produce peroxyesters in solution. The reaction mixture from the mixing zone is then taken to an agitated second-reaction zone where the reaction is completed preferably at a lower temperature. The product stream assaying greater than 95% is then recovered from the emulsion by employing settling units or centrifuges following the after reaction zone. The organic phase, then, may be subjected to a series of washes. One or a combination of the following solutions may be used for the washings: a buffered sulfite solution (that is, a solution of acetic acid, sodium acetate and sodium sulfite), saturated sodium bicarbonate, sodium hydroxide, potassium hydroxide, or the like. The washing steps are followed by physical separation of the emulsified aqueous and organic phases. These washing steps reduce trace impurities (the hydroperoxide and chloride) in the product. Further purification can be achieved by air drying in a packed column to reduce the moisture content to less than 500 PPM (part per million) and also remove other volatile impurities. The final product obtained is generally 98–99% or better in assay.

In order to carry out the peroxyesterification reaction in an efficient manner and to ensure complete conversion of the acid chloride, it is necessary to bring the aqueous and organic phases into intimate contact by vigorous agitation of the reaction mixture in the mixing zone; this vigorous agitation results in the emulsification of the reaction mass. An added advantage of this intense mixing is the tremendous enhancement of the heat transfer rate from the aqueous-organic system to the coolant in the coil and jacket. Hence, efficient dissipation of the heat of reaction with consequently improved temperature control and safety of operation are provided for in this invention.

The types of impellers that can be used for the intense agitation are a flat-blade turbine, a pitch-blade turbine or a marine type propeller. The size of the reactor and the dimensions of the impeller determine the speed of agitation. For example, in a ten gallon reactor of standard configuration (liquid depth to reactor diameter ratio equals 1 to 2) if the diameter of the impeller is 4 to 5 inches, 1000 to 1400 revolutions per minute (RPM) give sufficient agitation. Conventional agitation would provide for up to 5 horsepower (HP) per 1000 gallons. In the present invention, utilizing a reactor of standard configuration, it has been found that an impeller tip speed of at least 1000 feet per minute and a power input in the range of 50 to 200 horsepower per 1000 gallons is necessary to provide the intense mixing for high conversion and fast reaction.

The arrangement of the reactors and the feed system enables independent control of the raw material flow rates and the flexibility of introducing a solvent, if neccessary. Also in the reactors, the products of reactions themselves serve as a heat sink for the heat generated by the reaction. By efficient deployment of heat transfer surfaces, this heat is immediately absorbed from the system. Such an arrangement significantly improves the production capacity (throughput per unit volume of reactor) of the reactor system over the ones of the prior art. In the system employed in the reference patent, the production rate per unit reactor volume is 6 to 10 grams per gallon per hour of active oxygen (A(O)) content, whereas the equipment in this invention has a capacity of 80 to 120 grams per gallon per hour of (A(O)) content. By judicious choice of the reactant concentrations in the mixing zone, the conversion of the acid chloride to peroxyester can be promoted, while simultaneously minimizing acid chloride hydrolysis, leading to very high yields of product based on acid chloride consumed, thus making the process commercially attractive.

The invention will be better understood by reference to the drawing. The accompanying drawing is a schematic plan view of one form of apparatus suitable for practicing this invention.

The reactants are continuously added from storage tanks (1, 2 and 3) at controlled flow rates via metering devices (11, 12 and 13) to reactor (21). A major portion of the reaction (normally 90–95%) conversion of the acid chloride takes place in reactor (21) with the temperature of the reaction mixture being maintained within ±1° C of that desired (normally about 0° to 40° C). The reaction mixture (emulsion) from reactor 21 then flows continuously to the second reactor 22 where the remainder of the reaction occurs and where the temperature is preferably lowered to about −10° to +20° C since slight heating occurs during the vigorous agitation. Both reactors 21 and 22 are provided with efficient agitating means (9) and 7 to ensure thorough mixing of the reactants and cooling means 20 and 23 to remove the heat of reaction. Reactor 21 is also equipped with a pH meter (8) to regulate the pH of the reaction mixture in the range of 10 to 14 and preferable 10 to 12. Such a system ensures complete conversion of the acid chloride to peroxyester, thereby improving the product quality and yield considerably. Also the system achieves excellent temperature control resulting in consistent product quality and improved safety.

The cooled reaction mixture from reactor 22 is then continuously fed through separation device 33 such as a centrifuge or gravity settling unit, where the peroxyester product is separated as stream 26. The aqueous stream 25 is discarded. The product stream 26 of at least 95% purity can be collected at this point as a pure product. Alternatively, to improve its purity it can be processed further giving it a sequence of washes in a series of mixing-settling units 34. The temperature in the mixing vessel is maintained in the range of $-10°$ to $+20°$ C by cooling means. The product stream 36 from the final settling unit has an assay of at least about 98%; again the aqueous phase 37 is discarded.

If still further increase in purity to at least 99% assay is desired with a reduction of acid chloride, hydroperoxide and water, the product stream 36 from final settling device in the mixer-settler system 34 is continuously fed through a stripping column 38 where it is subjected to stripping with a stripping medium 39 of dry air or other oxygen containing gas at ambient temperatures. Column 38 is a conventional column containing plates or packing with either countercurrent or crossflow movement of the stripping medium 39 to the product stream 36. The product 41 can be either packed out as a pure material or diluted with various solvents such as dimethyl phthalate or odorless mineral spirits. When it is desirable to prepare a solution rather than the pure peroxyester, the solvent can be introduced at any point of the system. For example, storage tanks 4 or 5 may be used to introduce solvent into either reactors 21 or 22 via metering devices 14 or 15, respectively.

The acid chloride used in the process should have an assay of at least 90%, preferably greater than 95%. Hydroperoxides assaying 50–100%, preferably about 70% (when t-butyl hydroperoxide is used), and sodium or potassium hydroxide solution assaying 20–50% are advantageously employed as the other starting materials in the process. For monoperoxyesters the stoichiometric mole ratios of caustic to acid chloride and hydroperoxide to acid chloride are 1:1 and 1:1, respectively. In practice, however, depending on the peroxyester being formed, 10–90% excess base and 0–50% excess of hydroperoxide are used to promote complete conversion of the acid chloride.

The storage tanks 1,2,3,4 and 5 and metering controls 11,12,13,14 and 15 can be constructed of any type of materials compatible with the reactants to be stored or pumped. The mixing tanks in the mixing-settling system 34 can be of glass or stainless steel. Reactors 21 and 22 are preferably made of stainless steel. Centrifuges, if used in the process can be either liquid-solid or liquid-liquid centrifuges depending on whether the peroxyester is solid or liquid. Since most of the peroxyesters are liquid, the liquid-liquid centrifuges are normally used. Conventional centrifuges of either the basket, bowl or disc type can be employed. The centrifuges in the examples infra are the liquid-liquid centrifuges of the desludging disc type.

There are many advantages of the instant invention over the prior art:

1. The instant invention does not require a solvent in the reaction in order to be safe while the prior art does. If the prior art eliminates the solvent, products with high wetting points and high heats of reaction would be difficult or impossible to make. Hence, a solvent is essential in the systems of the prior art for safety and to maintain acceptable reaction conditions. In the instant invention a solvent is optional. Where pure, undiluted product is desired, no solvent is used.

2. The instant invention produces 7 to 10 times more output per reactor volume than the prior art.

3. The instant invention obtains a product of high purity by assay and low chloride content leaving the reaction zone.

4. The instant invention has a basic medium (pH greater than 10) while the prior art uses a neutral or acidic medium (pH of 7 or less). Hence in the instant invention the reactants are easier on the vessels of construction than the prior art.

5. The instant invention obtains a higher yield based on acid chloride used.

6. The instant invention can make a wider range of peroxyesters.

7. The instant invention does not pollute the atmosphere while the prior art system which uses air sparging to promote circulation would pollute the atmosphere with obnoxious fumes.

8. The instant invention is safer by not allowing product to accumulate in the reactors; the intense mixing eliminates the chance of producing hotspots.

9. The instant invention is more economic and commercially feasible.

The following examples are set forth to merely illustrate the invention but are not meant to limit the practice of this invention. Flow rates are in parts by weight per hour (pph) unless indicated.

The products set forth in the Examples in TABLE A were prepared by the following general procedure. The reactants were continuously introduced first into mixing reactor 21 at the specified flow rates and then into the second reactor 22. The pH of the reaction mixture in every example was maintained higher than 10. The mixing reactor 21 was maintained in the upper part of the required temperature range while the second reactor 22 was maintained in the lower part of the temperature range. Both reactors were vigorously agitated to ensure an intimate mixing for complete reaction. The mixing-settling-stripping separation system 33, 34 and 38 were used in all the Examples except for Example 1. Example 1 had an assay of 99% when it was recovered from the bottom of reactor 22. A solvent was used only in Examples IIIA and IV.

TABLE A

| Ex. | Reactants | Flow rate into mixing reactor in lbs/hr. | Temp. in mixing reactor in ° C. | Temp. in second reactor ° C | Separation system used | Solvent used | Product | Rate of product lb/hr | Assay of product in % | Yield based of acid chloride in % |
|---|---|---|---|---|---|---|---|---|---|---|
| | Benzoyl | | | | | | t-butyl | | | |

TABLE A-continued

| Ex. | Reactants | Flow rate into mixing reactor in lbs/hr. | Temp. in mixing reactor in °C. | Temp. in second reactor °C | Separation system used | Solvent used | Product | Rate of product lb/hr | Assay of product in % | Yield based of acid chloride in % |
|---|---|---|---|---|---|---|---|---|---|---|
| I | Chloride<br>25% NaOH<br>70% t-butyl hydroperoxide | 48<br>66<br>44 | 15°+1 | 10°+1 | No | None | perbenzoate | 60 | 99% | 91% |
| II | 2-ethyl-hexanoyl chloride<br>25% KOH<br>70% t-butyl hydroperoxide | 36<br>64<br>34 | 25°+1 | 15°+1 | Yes | None | t-butyl peroctoate | 48 | 99% | 96% |
| III | neodecanoyl chloride<br>35% KOH<br>70% t-butyl hydroperoxide | 32<br>45<br>30 | 40°+1 | 20° | Yes | None | t-butyl peroxy-neodecanoate | 40 | 98% | 86% |
| IIIA | same as III | | | | | mineral spirits 6 lbs/hr | t-butyl peroxy-neodecanoate | 40 | 80% | 90% |
| IV | Pivaloyl chloride<br>30% KOH<br>70% t-butyl hydroperoxide | 20<br>44<br>30 | 0° | −5° | Yes | odorless mineral spirits 9lbs/hr | t-butyl peroxy-pivalate | 42 | 75% | 88% |

The following is an example of the continuous preparation of a mixed diperoxyester from a diacid chloride using the apparatus as described.

EXAMPLE V

Preparation of a mixture of 4- and 5-(t-butylperoxycarbonyl)-3-hexyl-6-[7-(t-butylperoxycarbonyl)heptyl]cyclohexenes and 4- and 5-(t-butyl-peroxycarbonyl)-3-pentyl-6-[8-(t-butylperoxycarbonyl)octyl]cyclohexenes.

Potassium hydroxide (25% aqueous solution), t-butylhydroperoxide (70%) and a mixture of 4- and 5-chlorocarbonyl-3-hexyl-6-[7-(chlorocarbonyl) heptyl]-cyclohexenes and 4- and 5-chlorocarbonyl-3-pentyl-6-[8-(chlorocarbonyl)octyl]cyclohexenes are introduced into the mixing reactor (21), along with an aliphatic organic solvent (hexane, heptane etc.) at the rate of 36 lbs/hr, 20 lbs/hr and 20 lbs/hr 20 lbs/hr respectively. The temperature in the reaction zone (21) and the after reaction zone 22 are maintained at 5° C. The desired diperoxyester mixture is produced at a rate of about 20 lbs/hr assaying greater than 85%.

The continuous preparation of a diperoxyester from a dihydroperoxide and a monoacid chloride is described in Example VI below. In this case the dihydroperoxide is a solid and any conventional means for feeding a solid material to the mixing reactor 21 can be utilized.

EXAMPLE VI

Preparation of 2,5-Dimethyl-2,5-di(2-ethylhexanoylperoxy)hexane.

Sodium hydroxide (25% aqueous solution), 2-ethylhexanoyl chloride (93%), 2,5-dimethyl-2,5-dihydroperoxyhexane (70%) are introduced into the mixing reactor (21) along with an aliphatic organic solvent (hexane, heptane etc.) at the rate of 51 lbs/hr, 31 lbs/hr and 38 lbs/hr respectively. The temperature in the reaction zone 21 is maintained at about 30° C and that in the after reaction zone 22 at about 20° C. The product 2,5-dimethyl-2,5-di(2-ethylhexanoylperoxy)hexane is obtained at the rate of about 50 lbs/hr.

What is claimed is:

1. A process for the continuous manufacture of a peroxyester having the formula

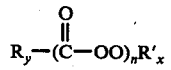

wherein:
(a) $x$, $y$, and $n$ are 1 or 2;
(b) when $x$ is 2, $y$ is 1 and $n$ is 2;
(c) when $y$ is 2, $x$ is 1 and $n$ is 2;
(d) when $x$, $y$ and $n$ are 1, R is selected from the group consisting of a primary, secondary, or tertiary alkyl of 1 to 17 carbons, aryl of 6 to 14 carbons, and cycloalkyl of 3 to 12 carbons, and R' is selected from the group consisting of a tertiary alkyl of 4 to 12 carbons, a tertiary aralkyl of 9 to 18 carbons, and tertiary cycloalkyl of 6 to 12 carbons;
(e) when $x$ is 2, R is a diradical selected from alkylene of 1 to 16 carbons, arylene of 6 to 14 carbons, cycloalkylene of 3 to 12 carbons, and aralkylene of 7 to 18 carbons; and
(f) when $y$ is 2, R' is a di-tertiary diradical selected from alkylene of 6 to 16 carbons, aralkylene of 12 to 18 carbons, and cycloalkylene of 7 to 12 carbons;
which comprises:
(I) continuously reacting an acid chloride having the formula

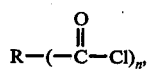

a hydroperoxide having the formula R'(OOH)$_n$, and an aqueous alkali metal hydroxide in two reaction zones of intense mixing connected in series in a temperature range of about −10° to +50° C and a pH of 10 to 14, wherein the first reaction zone is maintained in the upper part of the temperature range and the second reaction zone is maintained in the lower part of the temperature range;

(II) continuously recovering the peroxyester product by
  (i) continuously feeding the reaction mixture directly from the second reaction zone through a liquid-liquid separation unit;
  (ii) continuously subjecting the product stream from the liquid-liquid separation unit to a series of washings and separations in a mixer-settler system; and
  (iii) continuously gas stripping the product from the mixer-settler system in a stripping column; and
  (iv) continuously adding the acid chloride, hydroperoxide and aqueous alkali metal hydroxide to the first reaction zone to replace that used up in the reaction effluent.

2. The process of claim 1 wherein the throughput per unit volume of the reactor is 80 to 120 grams per gallon per hour of active oxygen content.

3. The process of claim 1 wherein R is t-butyl.

4. The process of claim 1 wherein R is phenyl.

5. The process of claim 1 wherein R is 3-heptyl.

6. The process of claim 1 wherein R is t-nonyl.

7. The process of claim 1 wherein R' is t-butyl.

8. The process of claim 3 wherein a solvent is added to the first reaction zone.

9. The process of claim 1 wherein the reaction zones have a liquid depth to reactor diameter ratio of 1 to 2, and the intense mixing is provided by an impeller with a tip speed of at least 1000 feet per minute and a power input in the range of 50 to 200 horsepower per 1000 gallons.

REEXAMINATION CERTIFICATE (390th)
United States Patent [19]
Wagle et al.

[11] B1 4,075,236
[45] Certificate Issued  Sep. 24, 1985

[54] CONTINUOUS MANUFACTURE OF PEROXYESTERS

[75] Inventors: Uday D. Wagle, Grand Island; Venkatram Ramdas, Tonawanda, both of N.Y.

[73] Assignee: Pennwalt Corporation, Philadelphia, Pa.

Reexamination Request:
No. 90/000,562, May 24, 1984

Reexamination Certificate for:
Patent No.: 4,075,236
Issued: Feb. 21, 1978
Appl. No.: 728,349
Filed: Sep. 30, 1976

[51] Int. Cl.$^4$ .................................... C07C 179/18
[52] U.S. Cl. ................... 260/453 RZ; 260/410.9 R
[58] Field of Search ................ 260/453 RZ, 410.9 R

[56] References Cited

U.S. PATENT DOCUMENTS

| | | | |
|---|---|---|---|
| 3,082,236 | 3/1963 | Mogeli et al. | 260/453 RZ |
| 3,117,166 | 1/1964 | Harrison | 260/453 RZ |
| 3,308,163 | 3/1967 | McKellin | 568/568 |
| 3,435,060 | 3/1969 | Johannes | 260/453 RZ |
| 3,595,898 | 7/1971 | Harvey et al. | 260/453 R |
| 3,849,468 | 11/1974 | Busseret | 260/463 |
| 3,869,489 | 3/1975 | Wagle et al. | 260/453 RZ |
| 3,950,375 | 4/1976 | McKee et al. | 260/463 |

Primary Examiner—Alan L. Rotman

[57] ABSTRACT

A continuous solvent-free process for the manufacturing of peroxyesters from an acid chloride, a hydroperoxide and an alkali metal hydroxide generates a pure product of good quality, high yields and throughput per unit volume of the reactor. The process comprises at least two reactors and a physical separation unit for separating the high purity product.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, and 9 are determined to be patentable as amended.

Claims 3-8, dependent on an amended claim, are determined to be patentable.

1. A process for the continuous manufacture of a peroxyester having the formula

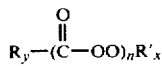

wherein:
- (a) x, y and n are 1 or 2;
- (b) when x is 2, y is 1 and n is 2;
- (c) when y is 2, x is 1 and n is 2;
- (d) when x, y and n are 1, R is selected from the group consisting of a primary, secondary, or tertiary alkyl of 1 to 17 carbons, aryl of 6 to 14 carbons, and cycloalkyl of 3 to 12 carbons, and R' is selected from the group consisting of a tertiary alkyl of 4 to 12 carbons, a tertiary aralkyl of 9 to 18 carbons, and tertiary cycloalkyl of 6 to 12 carbons;
- (e) when x is 2, R is a diradical selected from alkylene of 1 to 16 carbons, arylene of 6 to 14 carbons, cycloalkylene of 3 to 12 carbons, and aralkylene of 7 to 18 carbons; and
- (f) when y is 2, R' is a di-tertiary diradical selected from alkylene of 6 to 16 carbons, aralkylene of 12 to 18 carbons, and cycloalkylene of 7 to 12 carbons; which comprises:
  - (I) continuously reacting an acid chloride having the formula

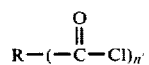

a hydroperoxide having the formula R'(OOH)$_n$, and an aqueous alkali metal hydroxide in two reaction zones of intense mixing connected in series in a temperature range of about −10° to +50° C. and a pH of 10 to 14, wherein the first reaction zone is maintained in the upper part of the temperature range and the second reaction zone is maintained in the lower part of the temperature range;
  - (II) continuously recovering the peroxyester product by
    - (i) continuously feeding the reaction mixture directly from the second reaction zone through a liquid-liquid separation unit;
    - (ii) continuously subjecting the product stream from the liquid-liquid separation unit to a series of washings and separations in a mixer-settler system; [and]
    - (iii) continuously gas stripping the product from the the mixer-settler system in a stripping column; and
    - (iv) continuously adding the acid chloride, hydroperoxide and aqueous alkali metal hydroxide to the first reaction zone to replace that used up in the reaction effluent.

2. [The] *A* process [of claim 1 wherein] *for the continuous manufacture of a peroxyester having the formula*

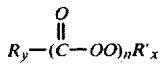

*wherein:*
- *(a) x, y and n are 1 or 2;*
- *(b) when x is 2, y is 1 and n is 2;*
- *(c) when y is 2, x is 1 and n is 2;*
- *(d) when x, y and n are 1, R is selected from the group consisting of a primary, secondary, or tertiary alkyl of 1 to 17 carbons, aryl of 6 to 14 carbons, and cycloalkyl of 3 to 12 carbons, and R' is selected from the group consisting of a tertiary alkyl of 4 to 12 carbons, a tertiary aralkyl of 9 to 18 carbons, and tertiary cycloalkyl of 6 to 12 carbons;*
- *(e) when x is 2, R is a diradical selected from alkylene of 1 to 16 carbons, arylene of 6 to 14 carbons, cycloalkylene of 3 to 12 carbons, and aralkylene of 7 to 18 carbons; and*
- *(f) when y is 2, R' is a di-tertiary diradical selected from alkylene of 6 to 16 carbons, aralkylene of 12 to 18 carbons, and cycloalkylene of 7 to 12 carbons; which comprises:*
  - *(I) continuously reacting an acid chloride having the formula*

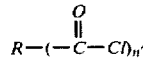

*a hydroperoxide having the formula R'(OOH)$_n$, and an aqueous alkali metal hydroxide in two reaction zones of intense mixing connected in series in a temperature range of about −10° to +50° C. and a pH of 10 to 14, wherein the first reaction zone is maintained in the upper part of the temperature range and the second reaction zone is maintained in the lower part of the temperature range;*
  - *(II) continuously recovering the peroxyester product by*
    - *(i) continuously feeding the reaction mixture directly from the second reaction zone through a liquid-liquid separation unit;*
    - *(ii) continuously subjecting the product stream from the liquid-liquid separation unit to a series of washings and separations in a mixer-settler system;* [and]
    - *(iii) continuously gas stripping the product from the mixer-settler system in a stripping column; and*
    - *(iv) continuously adding the acid chloride, hydroperoxide and aqueous alkali metal hydroxide to the first reaction zone to replace that used up in the reaction effluent,* the throughput per unit volume of the reactor [is] *being* 80 to 120 grams per gallon per hour of active oxygen content.

9. [The] *A* process [of claim 1 wherein] *for the continuous manufacture of a peroxyester having the formula*

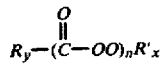

*wherein:*

*(a) x, y and n are 1 or 2;*
*(b) when x is 2, y is 1 and n is 2;*
*(c) when y is 2, x is 1 and n is 2;*
*(d) when x, y and n are 1, R is selected from the group consisting of a primary, secondary, or tertiary alkyl of 1 to 17 carbons, aryl of 6 to 14 carbons, and cycloalkyl of 3 to 12 carbons, and R' is selected from the group consisting of a tertiary alkyl of 4 to 12 carbons, a tertiary aralkyl of 9 to 18 carbons, and tertiary cycloalkyl of 6 to 12 carbons;*
*(e) when x is 2, R is a diradical selected from alkylene of 1 to 16 carbons, arylene of 6 to 14 carbons, cycloalkylene of 3 to 12 carbons, and aralkylene of 7 to 18 carbons; and*
*(f) when y is 2, R' is a di-tertiary diradical selected from alkylene of 6 to 16 carbons, aralkylene of 12 to 18 carbons, and cycloalkylene of 7 to 12 carbons; which comprises:*

*(I) continuously reacting an acid chloride having the formula*

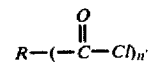

*a hydroperoxide having the formula R'(OOH)$_n$, and an aqueous alkali metal hydroxide in two reaction zones of intense mixing connected in series in a temperature range of about $-10°$ to $+50°$ C. and a pH of 10 to 14, wherein the first reaction zone is maintained in the upper part of the temperature range and the second reaction zone is maintained in the lower part of the temperature range,* the reaction zones [have] *having* a liquid depth to a reactor diameter ratio of 1 to 2, and the intense mixing [is] *being* provided by an impeller with a tip speed of at least 1000 feet per minute and a power input in the range of 50 to 200 horsepower per 1000 gallons;

*(II) continuously recovering the peroxyester product by*
*(i) continuously feeding the reaction mixture diectly from the second reaction zone through a liquid-liquid separation unit;*
*(ii) continuously subjecting the product stream from the liquid-liquid separation unit to a series of washings and separations in a mixer-settler system;* [and]
*(iii) continuously gas stripping the product from the mixer-settler system in a stripping column; and*
*(iv) continuously adding the acid chloride, hydroperoxide and aqueous alkali metal hydroxide to the first reaction zone to replace that used up in the reaction effluent.*

* * * * *